United States Patent [19]

Bergman

[11] Patent Number: 4,641,823
[45] Date of Patent: Feb. 10, 1987

[54] CRADLE DRIVE AND RELEASE MECHANISM FOR USE WITH A MAGNETIC RESONANCE SCANNER

[75] Inventor: Charles T. Bergman, Watertown, Wis.

[73] Assignee: General Electric Company, Milwaukee, Wis.

[21] Appl. No.: 683,081

[22] Filed: Dec. 18, 1984

[51] Int. Cl.⁴ .............................................. A61G 13/00
[52] U.S. Cl. ......................................... 269/322; 74/37
[58] Field of Search ........................... 74/37; 198/748; 378/208, 209, 177; 108/137, 143; 14/69.5, 71.1; 269/322, 323, 61; 254/95, 97

[56] References Cited

U.S. PATENT DOCUMENTS

| | | | |
|---|---|---|---|
| 4,227,421 | 10/1980 | Weishew | 74/37 |
| 4,262,204 | 4/1981 | Mirabella | 378/209 |
| 4,281,556 | 8/1981 | Weishew | 74/37 |
| 4,475,072 | 10/1984 | Schwehr et al. | 378/209 |
| 4,545,571 | 10/1985 | Chambron | 378/209 |
| 4,552,347 | 11/1985 | Wallis | 378/209 |

Primary Examiner—Robert C. Watson
Attorney, Agent, or Firm—Alexander M. Gerasimow; Douglas E. Stoner

[57] ABSTRACT

There is provided a cradle drive apparatus for releasably engaging and for retrievably positioning a patient cradle in an advanced position on a bridge within the bore of an MR scanner and for returning the patient cradle to a home position on a patient transport table. The apparatus includes a cradle drive dolly disposed on the bridge for longitudinal movement thereon. A clutch disc is mounted on the dolly which also supports a clutch pad and bias means for enabling the clutch pad to frictionally engage the clutch disc. The clutch disc is fixedly secured to a drive sprocket which engages a drive belt. A motor is coupled to the drive belt to bidirectionally drive the cradle drive dolly on the bridge when the clutch pad frictionally engages the clutch disc and when the motor is energized.

13 Claims, 3 Drawing Figures

FIG. 1

CRADLE DRIVE AND RELEASE MECHANISM FOR USE WITH A MAGNETIC RESONANCE SCANNER

BACKGROUND OF THE INVENTION

This invention relates to a magnetic resonance (MR) scanner apparatus. More specifically, this invention relates to a cradle drive and release mechanism for use with an MR scanner to retrievably position a patient cradle in the bore of a magnet and for returning the cradle to a home position on top of a patient transport table.

The magnetic resonance phenomenon has been utilized in the past in high resolution MR spectroscopy instruments by structural chemists to analyze the structure of chemical compositions. More recently, MR has been developed as a medical diagnostic modality having application in imaging the anatomy, as well as in performing in vivo, non-invasive spectroscopic analysis. As is now well known, the MR resonance phenomenon can be excited within a sample object, such as a human patient, positioned in a homogeneous polarizing magnetic field, by irradiating the object with radio frequency (RF) energy at the Larmor frequency. In medical diagnostic applications, this is typically accomplished by positioning the patient to be examined in the field of an RF coil having a cylindrical geometry, and energizing the RF coil with an RF power amplifier. Upon cessation of the RF excitation, the same or a different RF coil is used to detect the MR signals emanating from the patient volume lying within the field of the RF coil. The MR signal is usually observed in the presence of linear magnetic field gradients used to encode spatial information into the signal. In the course of a complete MR scan, a plurality of MR signals are typically observed. The signals are used to derive MR imaging or spectroscopic information about the object studied.

A whole-body MR scanner used as a medical diagnostic device includes a magnet, frequently of solenodial design, to produce the polarizing magnetic field. The bore of the magnet is made sufficiently large to accommodate RF, gradient, and shim coil assemblies, as well as the torso of a patient to be examined. The scanner also includes a table which supports a cradle used to retrievably position a patient within the bore of the magnet. The table is aligned longitudinally with the bore of the magnet and disposed at the same height to facilitate advancement of the cradle between a home position when the cradle is on the table and an advanced position when the cradle is in the magnet. Advancement of the cradle between the advanced and home position is accomplished using a cradle drive system located near the magnet.

The cradle drive system in an MR diagnostic system must be comprised of materials which are non-magnetic, non-conductive, non-hydroscopic, and non-MR active to avoid interference with the imaging process. The cradle drive system needs to be capable of power driven as well as manual operation. Manual operation is useful for either emergency removal of the patient or for aligning the patient prior to scanning. The maximum force that the cradle drive can exert when power driven should not exceed a predetermined adjustable limit of, for example, 30 pounds. This requirement ensures that the cradle drive is effectively disengaged in the event travel in either direction is obstructed. This feature is also useful in the event it is desired to manually override the power drive. The cradle drive system must also be capable of easily engaging and disengaging the patient cradle.

It is, therefore, a principal object of the invention to provide a cradle drive system having the above-noted features.

SUMMARY OF THE INVENTION

There is provided in accordance with the invention a cradle drive apparatus for releasably engaging and for retrievably positioning a patient cradle in an advanced position on a bridge within the bore of an MR scanner and for returning the patient cradle to a home position on a patient transport table. The apparatus includes a cradle drive dolly disposed on the bridge for longitudinal movement thereon. A clutch disc is mounted on the dolly which also supports a clutch pad and bias means for enabling the clutch pad to frictionally engage the clutch disc. The clutch disc is fixedly secured to a drive sprocket which engages a drive belt. A motor is coupled to the drive belt to bidirectionally drive the cradle drive dolly on the bridge when the clutch pad frictionally engages the clutch disc and when the motor is energized.

BRIEF DESCRIPTION OF THE DRAWINGS

The features of the invention believed to be novel are set forth with particularity in the appended claims. The invention itself, however, both as to its organization and method of operation, together with further objects and advantages thereof, may best be understood by reference to the following description taken in conjunction with the accompanying drawings in which:

FIG. 1 depicts a partial sectional view of an MR system including the inventive cradle drive and release system;

DETAILED DESCRIPTION OF THE INVENTION

Figure 1:
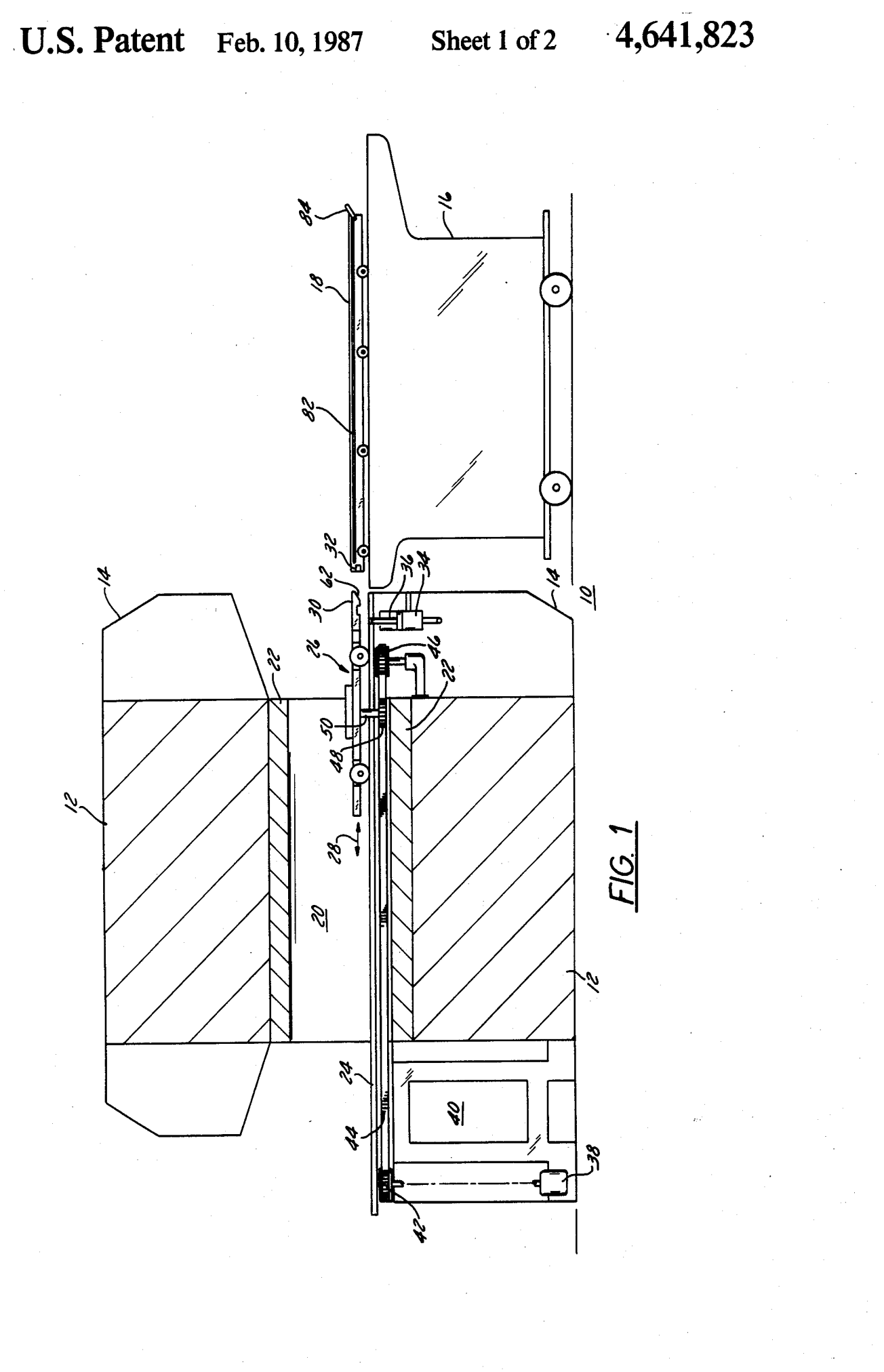
Figure 2:
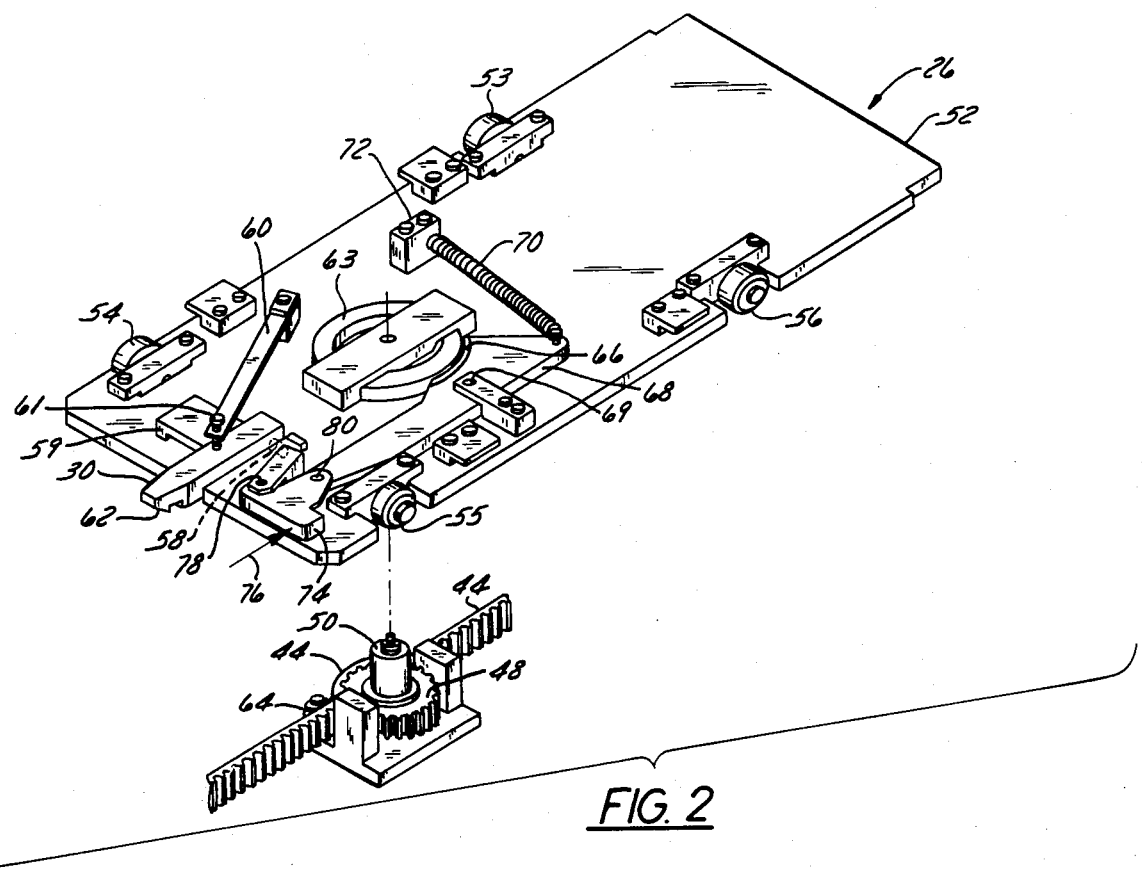
FIG. 2 is a perspective view of a cradle drive dolly which is part of the cradle drive system.

FIG. 1 depicts an MR system, generally designated 10, which includes a magnet 12 situated in a housing 14 and a mobile patient transport table 16 having a patient cradle 18 positioned thereon. Magnet 12, shown in cross section, is configured as a cylinder having a bore 20. A coil assembly 22, comprised of shim, gradient, and radio frequency coils, is disposed coaxially within the bore which is sized to receive patient cradle 18 and the patient (not shown) supported thereon. A bridge structure 24, which extends beyond the ends of the magnet, is provided within the bore for supporting the weight of the patient during a scan.

Continuing with reference to FIG. 1, the cradle drive and release system includes a cradle drive dolly 26 adapted for bidirectional travel on the bridge, as suggested by arrow 28. The dolly is equipped with a hitch 30 which engages a dolly hitch pin 32, located at the forward end of patient cradle 18, when the latter is to be advanced into the bore. A hydraulically operated cylinder 34, mounted to housing 14, is provided with a normally extended plunger 36 which acts against hitch 30 (when the cylinder is deactivated) to disengage the drive dolly from the patient cradle at the conclusion of a scan.

The cradle drive dolly is energized for bidirectional movement by a DC servomotor 38 mounted in a frame 40 located at the end of the magnet opposite to that used for receiving the patient. The motor output is coupled to a drive sprocket 42 which engages a cogged drive belt 44 situated below bridge 24 and which engages an idler sprocket 46 disposed at the patient receiving end of the magnet. The cogged belt additionally engages a drive sprocket 48 mounted to the cradle drive dolly by a shaft 50 and physically located below the bridge in line with sprockets 42 and 46. The drive dolly is advanced in one of the directions indicated by arrow 28, depending on the direction in which the belt is driven, as described hereinafter.

The construction of cradle drive dolly 26 will be described next in greater detail with reference to FIG. 2 in which elements described with reference to FIG. 1 are assigned like reference numbers. Referring now to FIG. 2, the drive dolly is made up of a flat plate member 52 provided with wheels 53-56 to enable the dolly to roll on the bridge. Hitch 30 is pivotally mounted to member 52 by a pivot rod 58 and is biased in its detent position against a block 59 by a flexible member 60 having a threaded bolt 61 at its end for adjusting the bias force. The forward end of the hitch is provided with a wedged surface 62 to enable the dolly to automatically engage dolly hitch pins 32 (FIG. 1) on the patient cradle. The force exerted by flexible member 60 against the hitch ensures reliable coupling between the drive dolly and the patient cradle.

Referring again to FIG. 2, a clutch disc 63 is rotatably mounted to member 52 at approximately the center thereof. The clutch disc is fixedly fastened to one end of shaft 50, while drive sprocket 48 is fixedly fastened to the other end of the shaft, although for clarity of illustration sprocket 48 and shaft 50 are shown separated from clutch disc 63. A pair of idler pulleys, such as pulley 64 visible in FIG. 2, ensures tight coupling between the cogged belt and drive sprocket 48. A clutch pad 66, mounted to a lever member 68 pivoted at a pivot 69, is applied against the edge of clutch disc 63 by a bias spring 70 attached at one end to a block 72 and at its other end to the lever. The frictional force between the clutch disc and clutch pad is sufficiently strong to prevent the clutch disc (and, hence, sprocket 48) from rotating when cogged belt 44 is driven. In this manner, the belt engages sprocket 44 and drives the cradle dolly. The tension on spring 70 is, however, adjusted so that the frictional force is limited to, for example, 30 pounds. If, for any reason, free movement of the dolly or the cradle is impeded, the clutch will slip, preventing any possible damage. The frictional force is selected to be relatively low so that the patient cradle could be manually withdrawn from the bore. This would be accomplished by pulling on the patient cradle until the clutch slips allowing the cradle to move.

For normal manual operation, however, the clutch pad is disengaged by applying pressure to a rocker member 74 at a point indicated by arrow 76. Rocker 74 is pivoted at a point 78 and pivotally attached to one end of lever 68 at a point 80 such that pressure at the indicated point causes the lever to rotate about point 69 to move the clutch pad away from the clutch disc. With the clutch pad disengaged, the clutch disc and drive sprocket assembly is free to run along belt 44, allowing the cradle to be manually moved in and out of the bore.

One way of applying force to rocker 74 is by means of a push rod 82 operated by lever 84, as shown in FIG. 1. It should be noted, however, that in normal operation clutch pad 66 engages clutch disc 63 and the cradle is power driven.

Figure 3:
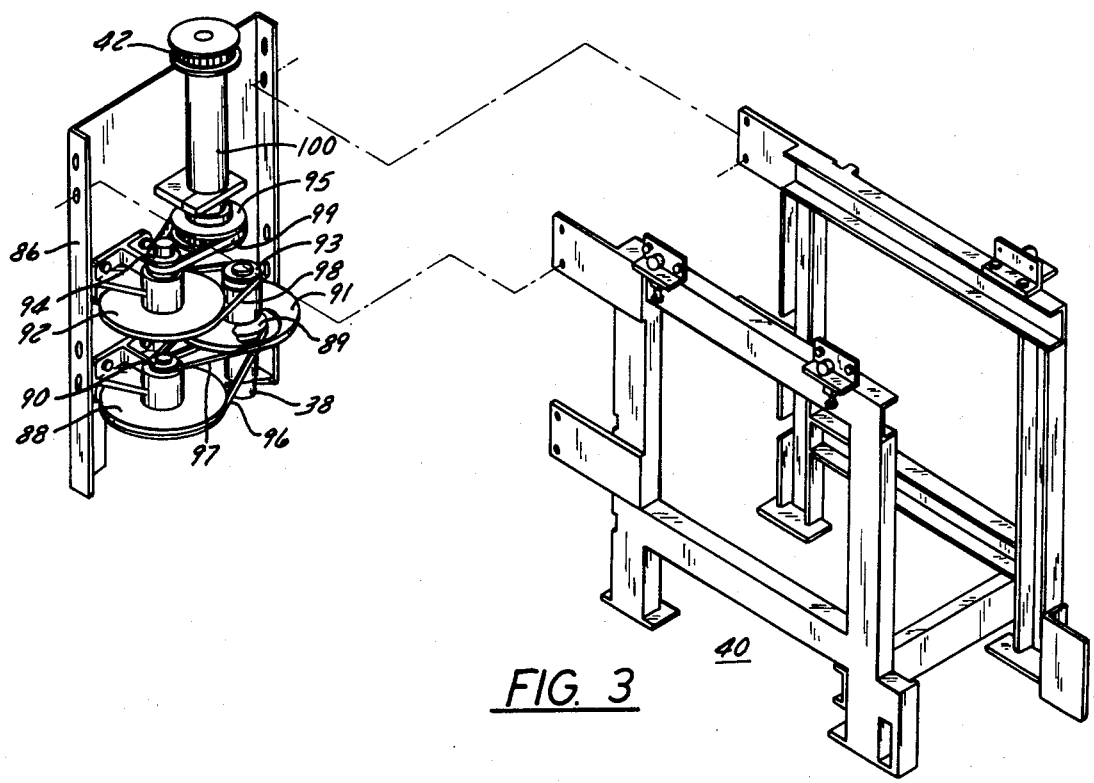
FIG. 3 depicts an exemplary power drive system used with the inventive cradle drive system.

FIG. 3 illustrates in greater detail the construction of frame 40 which supports bridge 24, DC servometer 38 and sprocket 42, as initially described with reference to FIG. 1. Continuing with reference to FIG. 3, the servomotor is mounted to the lower part of an end plate member 86, mounted to the end of frame 40, and is coupled to sprocket 42, mounted to the upper part of the end plate, by means of a pulley train comprised of pulleys 88-95 and drive belts 96-99. Pulley 92 is provided with a sprocket 94 which engages a sprocket 95, coupled to sprocket 42 by a shaft 100 by means of a cogged belt 99. It will be recognized that the servomotor may be coupled to sprocket 42 in a manner other than specifically described. The desired result is to reduce to output speed of the servomotor from, for example, 1500 rpm to 15 rpm.

In the preferred embodiment, a DC servomotor is used because it has been found to operate satisfactorily in the highly magnetic environment in the vicinity of the magnet. The main magnet (12, in FIG. 1), for example, in a whole-body MR scanner can have a magnetic field strength of 1.5 Tesla (15,000 Gauss) in the bore. The fringe magnetic field extends away from the magnet making it necessary to position both ferromagnetic and conductive objects (such as electric motors) away from the magnet to avoid disturbing the homogeneity of the magnetic field since this can adversely affect image quality. It is for this reason that the servomotor is mounted to the lower portion of end plate 86, as far as practical from the bore of the magnet. The fringe field in the vicinity of the servomotor is approximately 700 Gauss (if magnet 12 has a field strength of 1.5 T and a 1 meter bore diameter). At fringe field strengths above 700 Gauss, it has been found that conventional induction motors do not operate reliably. Direct current servomotors have been found to operate satisfactorily under these conditions. A particular servomotor which has been successfully used is manufactured by Electco Craft Corp. of Hopkins, Minn. and bears model designation E54ZA.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. A cradle drive apparatus for releasably engaging and for retrievably positioning a patient cradle in an advanced position on a bridge within the bore of an MR scanner and for returning the patient cradle to a home position on a patient transport table, said cradle drive apparatus comprising:
   a cradle drive dolly disposed on said bridge for longitudinal movement thereon;
   a clutch disc mounted on said drive dolly;
   a clutch pad and bias means for enabling said clutch pad to frictionally engage said clutch disc, said clutch disc fixedly secured to a drive sprocket means;
   drive belt means for engaging said drive sprocket means; and bidirectional motor operably coupled to said drive sprocket means to drive said cradle dolly on said bridge in a first direction when said clutch pad frictionally engages said clutch disc and when said motor means is energized to rotate in one direction, and to drive said cradle dolly in a second direction, opposite to said first direction, when said motor means is energized to rotate in the opposite direction.

2. The cradle drive apparatus of claim 1 wherein said motor means comprises a direct current servomotor.

3. The cradle drive apparatus of claim 1 wherein said clutch disc is rotatably mounted to said cradle drive dolly and further comprising means for disengaging said clutch disc from said clutch pad, said clutch disc and drive sprocket being free to rotate along said drive belt means when said clutch disc and pad are disengaged allowing said cradle dolly to be easily moved by manual effort.

4. The cradle drive apparatus of claim 1 wherein said clutch pad is selectively biased against said clutch disc so as to produce a predetermined frictional force therebetween such that when said frictional force is exceeded said clutch pad and disc slip relative to one another preventing further movement of said cradle drive dolly on said bridge under the influence of said motor means.

5. The cradle drive apparatus of claim 1 wherein said motor means comprises a direct current servomotor.

6. The cradle drive apparatus of claim 1 wherein said clutch disc is rotatably mounted to said cradle drive dolly and further comprising means for disengaging said clutch disc from said clutch pad, said clutch disc and drive sprocket being free to rotate along said drive belt means when said clutch disc and pad are disengaged allowing said cradle dolly to be easily moved by manual effort.

7. The cradle drive apparatus of claim 1 wherein said cradle drive dolly further comprises means for releasably engaging said patient cradle and hydraulically activated means for disengaging said means for releasably engaging from said patient cradle.

8. A cradle drive apparatus for releasably engaging and for retrievably positioning a patient cradle in an advanced position on a bridge within the bore of an MR scanner and for returning the patient cradle to a home position on a patient transport table, said cradle drive apparatus comprising:
a cradle drive dolly disposed on said bridge for longitudinal movement thereon, including means for releasably engaging said patient cradle and means for disengaging said means for releasably engaging from said patient cradle;
a clutch disc mounted on said drive dolly;
a clutch pad and bias means for enabling said clutch pad to frictionally engage said clutch disc, said clutch disc fixedly secured to a drive sprocket means;
drive belt means for engaging said drive sprocket means; and
motor means operably coupled to said drive sprocket means to bidirectionally drive said cradle dolly on said bridge when said clutch pad frictionally engages said clutch disc and when said motor means is energized.

9. The cradle drive apparatus of claim 8 wherein said means for disengaging comprises hydraulically activated means.

10. The cradle drive apparatus of claim 8 wherein said motor means comprises a direct current servomotor.

11. The cradle drive apparatus of claim 8 wherein said clutch disc is rotatably mounted to said cradle drive dolly and further comprising means for disengaging said clutch disc from said clutch pad, said clutch disc and drive sprocket being free to rotate along said drive belt means when said clutch disc and pad are disengaged allowing said cradle dolly to be easily moved by manual effort.

12. The cradle drive apparatus of claim 8 wherein said clutch pad is selectively biased against said clutch disc so as to produce a predetermined frictional force therebetween such that when said frictional force is exceeded said clutch pad and disc slip relative to one another preventing further movement of said cradle drive dolly on said bridge under the influence of said motor means.

13. A cradle drive apparatus for releasably engaging and for retrievably positioning a patient cradle in an advanced position on a bridge within the bore of an MR scanner and for returning the patient cradle to a home position on a patient transport table, said cradle drive apparatus comprising:
a cradle drive dolly disposed on said bridge for longitudinal movement thereon, including means for releasably engaging said patient cradle and means for disengaging said means for releasably engaging from said patient cradle;
a clutch disc mounted on said drive dolly;
a clutch pad and bias means for enabling said clutch pad to frictionally engage said clutch disc, said clutch disc fixedly secured to a drive sprocket means;
drive belt means for engaging said drive sprocket means;
motor means operably coupled to said drive sprocket means to bidirectionally drive said cradle dolly on said bridge when said clutch pad frictionally engages said clutch disc and when said motor means is energized; and
wherein said clutch pad is biased against said clutch disc so as to produce a predetermined frictional force therebetween such that when said frictional force is exceeded said clutch pad and disc slip relative to one another preventing further movement of said cradle drive dolly on said bridge under the influence of said motor means.

* * * * *